United States Patent [19]
Kronick et al.

[11] Patent Number: 6,054,266
[45] Date of Patent: Apr. 25, 2000

[54] NUCLEIC ACID DETECTION WITH SEPARATION

[75] Inventors: Mel N. Kronick, Palo Alto; Douglas H. Keith, Oakland; Lincoln J. McBride, Redwood City; Norman M. Whiteley; Michael W. Hunkapiller, both of San Carlos, all of Calif.

[73] Assignee: Applied Biosystems, Inc., Foster City, Calif.

[21] Appl. No.: 07/276,139

[22] Filed: Nov. 23, 1988

Related U.S. Application Data

[63] Continuation-in-part of application No. 07/135,652, Dec. 21, 1987, abandoned.

[51] Int. Cl.$^7$ .............................. C12Q 1/68; C07H 21/04
[52] U.S. Cl. ...................... 435/6; 435/7.72; 536/23.1; 536/24.2; 536/24.31; 536/24.32
[58] Field of Search ..................... 435/6, 7.72; 536/23.1, 536/24.2, 24.31, 24.32

[56] References Cited

U.S. PATENT DOCUMENTS

| | | |
|---|---|---|
| 135,652 | 12/1873 | Kronick et al. . |
| 4,613,566 | 9/1986 | Potter .......................................... 435/6 |
| 4,672,040 | 6/1987 | Josephson ................................ 436/526 |

FOREIGN PATENT DOCUMENTS

| | | |
|---|---|---|
| 0017373 | 1/1984 | European Pat. Off. . |
| 0237833 | 2/1987 | European Pat. Off. . |
| PCT/US84/ 00508 | 4/1984 | WIPO . |
| 8605519 | 9/1986 | WIPO ....................................... 435/6 |

OTHER PUBLICATIONS

Manning, et al., *Biochemistry* (1977) 16:1364–1370.
Honigberg, et al., *Proc. Natl. Acad. Sci. USA* (1986) 83:9586–9590.
Jones, et al., *Gene* (1985) 39:77–83.
Kempe, et al., *Nucleic Acids Res.* (1985) 13:45–57.
Gamper, et al., *Nucleic Acids Res.* (1986) 14:9943–9954.
Zapolski, et al., *Electrophoresis* (1987) 8:255–261.
Goldkorn, et al., *Nucleic Acids Res.* (1986) 14:9171–9191.
Syvänen, et al., *Nucleic Acids Res.* (1986) 14:5037–5048.
Forster, et al., *Nucleic Acids Res.* (1985) 13:745–761.
Moser, et al., *Science* (1987) 238:645–650.
Sluka, et al., *Science* (1987) 238:1129–1132.
Saiki, et al., *Science* (1985) 230:1350–1354.
Dervan, *Science* (1986) 232:464–471.
Herman, et al., *Anal. Biochem.* (1986) 156:48–55.
Charmichael, et al., *Methods of Enzym.* (1980) 65:380–391.
Draper in *Nucleic Acids Res.* (1984) 12:989–1002.
Feinberg, et al., *Anal. Biochem.* (1983) 132:6–13 and 137:266–267 (1984).
Southern, et al., *J. Mol. Biol.* (1975) 98:503–517.
Thompson, *BioChromatography* (1987) 2:4–6, 10–14, 16–18.
Vector Laboratories literature, "PHOTOPROBE™ Biotin" (1985).

*Primary Examiner*—George C. Elliott
*Attorney, Agent, or Firm*—Cooley Godward LLP

[57] ABSTRACT

Nucleic acid sequences are detected by a multi-step process, involving labeling sample nucleic acid sequences, duplexing the labeled sample with a probe having a coupling element, immobilizing all of the duplexed probe and target sequence and unduplexed probe, separating specifically immobilized nucleic acid from free and non-specifically immobilized nucleic acid, releasing specifically immobilized nucleic acid, and detecting the presence of the sequence of interest by means of the label. The labeled sequence may be characterized by sizing, e.g. electrophoresis. The method provides for a sensitive and rapid means for accurate detection of sequences of interest in a wide variety of situations.

19 Claims, No Drawings

NUCLEIC ACID DETECTION WITH SEPARATION

This Application is a Continuation-in-part of U.S. patent application Ser. No. 07/135,652, filed Dec. 21, 1987, now abandoned.

TECHNICAL FIELD

Detection of nucleic acid sequences employing probes for high sensitivity.

BACKGROUND

Today, biology is in many ways the science of proteins and nucleic acids. Nucleic acids are found in all living matter. For each species or host, unique sequences exist providing for the genotype and phenotype of that particular host. Thus, one can use the presence of a particular sequence as indicative of the particular strain or species. In many instances, a number of strains will share a common sequence as distinct from other strains or species, so that one can not only detect a particular strain but, if desired, can detect subspecies, species or genera. In addition, one can distinguish between RNA or DNA so as to determine whether a particular gene is being expressed, the existence of one or more alleles, the level of expression, and the like. Where cells, such as B-cells and T-cells, are involved with genomic rearrangements, one can detect the presence or absence of such rearrangements by employing probes. Thus, the detection of particular nucleic acid sequences is a powerful tool in the diagnosis of disease states, the presence of sets or subsets of cells, the particular strain or species of a pathogen, such as a bacterium, protista, or virus, or the like.

The detection and isolation of sequences is also important in the field of molecular biology. Thus, the use of probes allows for detection of a variety of sequences of interest, including structural genes, regulatory sequences, introns, exons, leader sequences, both translated and untranslated, and the like.

There is also substantial interest in detecting sequences in genetic engineering. Monitoring levels of transcription, detecting the integrity of constructs, monitoring levels of mutation, resection, or the like provide opportunities for nucleic acid screening and detection.

In many instances, the sequence of interest may be present as only a very small fraction of the total amount of nucleic acid, and/or in very small amount, e.g. attomole levels. Furthermore, the sequence of interest may be accompanied by a number of sequences having substantial homology to the sequence of interest. Thus, relatively high stringencies may be required to ensure the absence of unwanted heteroduplexing, which may further limit the available concentration of the sequence of interest.

Additionally, the same or similar sequences may appear on nucleic acid fragments of different size and the appearance of a sequence on a particular size fragment may be correlated to the presence of a particular phenotype. The usual procedure for such analyses, a Southern blot, is performed often but has certain inherent problems. Many manual manipulations are required including handling of fragile gels and membranes during the blotting step. Hybridization in a Southern blot occurs on filters which can slow down reaction rates, be sources of high background, and require large volumes of probe solutions (often highly radioactive) and large wash volumes.

There is also interest in developing analytical systems which can be automated, so as to minimize the time and energy required from technicians, as well as minimizing errors which may result from manual manipulation. Other considerations include the ability to provide a sample which allows for size determination, particularly for ease of detection of bands in conjunction with standards.

RELEVANT LITERATURE

EPA 0 237 833 describes a solution phase hybridization assay. Southern, *J. Mol. Biol.* (1975) 98:503–517 describes the original method for hybridization analysis of restriction fragments that have been transferred to filters. Manning, et al., *Biochemistry* (1977) 16:1364–1370 describe a method for gene enrichment based on the avidin-biotin interaction. Thompson, *BioChromatography* (1987) 2:68–79 describes the use of high performance liquid chromatography for separation of nucleic acid fragments. Jones et al., *Gene* (1985) 39:77–83 describe electrophoretic separation and subsequent detection of RNA:DNA hybrids. Persons and Finn, *BioTechniques* (1986) 4:404–406 describe an immunoadsorption procedure to analyze low abundance polypeptides. Kempe et al., *Nucl. Acids. Res.* (1985) 13:45–57 describe biotinylated oligonucleotides linked to DNA fragments by a ligase. Gamper et al., *Nucl. Acids Res.* (1985) 14:9943–9954, employs a psoralen-functionalized oligomer as a probe which labels target DNA when hybridization and photochemical cross-linking occur. Zapolski et al. Electrophoresis (1987) 8:255–261 discuss a robotic system for automating Southern-type nucleic acid hybridization analysis. Goldkorn and Prockop, *Nucl. Acids Res.* (1986) 14:9171–9191 describe techniques for covalent attachment of DNA probes to cellulosic supports for hybridization-restriction analysis. Syvanen et al., *Nucl. Acids Res.* (1986) 14:5037–5048 quantify nucleic acid hybrids by affinity-based hybrid collection. Forster et al., *Nucl. Acids Res.* (1985) 13:745–761 covalently label nucleic acids with biotin photochemically. Blakesley and Thompson, PCT/US84/00508 (WO 85/04674) discuss novel techniques for immobilization of nucleic acids. Gamper et al., *Nucleic Acids Res.* (1986) 14:9943–9954 describes a reverse Southern hybridization. Honigberg et al., *Proc. Natl. Acad. Sci.* USA (1986) 83:9586–9590 describes the use of recA protein to search for rare sequences of duplex DNA.

SUMMARY OF THE INVENTION

Nucleic acid sequences are detected and sized by employing a probe having a solid support linking element. A nucleic acid sample is labeled and the labeled chains may be conveniently provided in single-stranded form and hybridized with the probe. Duplexes and excess probe are separated by means of a solid entity, providing a liquid phase which may be retained and used for further assays, and a solid phase with which the duplex sample may be detected, isolated and sized, e.g. electrophoretically.

In an alternative configuration, a probe is combined with recA protein followed by sequence-specific complex formation with labeled target sequences. Complexes and excess probe are then employed as described above.

DESCRIPTION OF THE SPECIFIC EMBODIMENTS

Methods and compositions are provided for detecting the presence of a nucleic acid sequence in a sample. The method involves employing a detection entity and a coupling entity, where the sample nucleic acid is labeled with a detection entity and the coupling entity is bound to the probe. Complexed sample nucleic acid and probe are separated from uncomplexed sample nucleic acid by means of a solid component. The duplex of sample nucleic acid and probe may then be separated from the solid component (by chemical cleavage or denaturation) and the labeled sample nucleic acid manipulated as desired, e.g. sized and detected.

The source of the sample may be any material or substance comprising nucleic acid. The nucleic acid need not be a naturally occurring nucleic acid, but may be synthesized chemically, enzymatically, or biologically and may have other than naturally occurring purines and pyrimidines. The sample source may be cellular or non-cellular, may be a clinical sample or isolate, may be derived from such physiological media as blood, serum, plasma, stool, pus, scrapings, washings, urine, or the like; may be associated with a set or subset of cells, such as neoplastic cells, lymphocytes, e.g. T-cells or B-cells, monocytes, neutrophils, etc.; pathogens, including viruses, bacteria, mycoplasma, fungi, protozoa, etc.; may include constructs, involving plasmids, viruses or DNA or RNA fragments, or the like. The nucleic acid sample may involve DNA, which may be chromosomal or extrachromosomal, e.g. plasmids, viruses, synthetic constructs, etc. or RNA, such as messenger RNA, transfer RNA, ribosomal RNA, viruses, or the like. The nucleic acid sequences may involve structural genes, untranslated regions, regulatory regions, introns, exons, or the like.

The detection may be for a wide variety of purposes. Detection may involve diagnosis of a diseased state in plant or animal species, such as neoplasia or other aberrant cellular state, the detection of sets or subsets of cells, such as lymphocytes at various stages of differentiation, the detection of strains or species of pathogens, the monitoring of genetic engineering, or the like. Prior to use of the sample in the subject invention, the sample may have been subjected to a variety of chemical or physical treatments, such as proteolysis, extraction, precipitation, separation of nucleic acid from other components, such as lipids, proteins, or the like, hydrolysis of RNA, inactivation of nucleases, concentration, chromatography, dehydration, heating, etc. The sample may be manipulated for a variety of reasons, such as removal of interfering materials, preparation for storage or shipment, concentration, or the like.

In many instances, particularly where the sample involves large nucleic acid molecules, the composition will normally be subjected to fragmentation, particularly employing restriction enzymes. One or more restriction enzymes may be employed where, depending upon the nature of the sample, fragments may be provided varying from 50 bp to 100 kbp, more usually from about 0.5 to 25 kbp. Various restriction enzymes may be used resulting in the formation of flush or sticky ends. In some situations, the presence of sticky ends may be desired as a specific site for linking.

In some instances, the sample may involve the reverse transcription product of messenger RNA, where the mixture may be relatively small sequences of DNA and RNA. If desired, the RNA may be hydrolyzed, leaving only the DNA sequences. In this manner, one would have a composition of solely single-stranded DNA.

Once the sample has been pre-prepared, it is now ready for labeling. Labeling can be achieved in a wide variety of ways. While the particular manner of labeling is not critical, and will depend upon a number of considerations, there are preferred techniques because of efficiency, sensitivity, economics and the like. One consideration will be the sensitivity of detection employing the label, the manner in which the nucleic acid sequence is to be subsequently treated or analyzed, and the like.

The chains may be extended by various techniques, depending to some degree on whether the chains are single- or double-stranded. The chains may be extended at the 3'-termini by using terminal deoxytransferase, where the additional nucleotides may be labeled in a variety of ways, for example by using radioactively labeled nucleotides or nucleotides labeled by other moieties.

With double-stranded DNA, various molecules may be employed having complementary ends, e.g. short double-stranded sequences, particularly with cohesive ends either produced by restriction enzymes or identical to such ends, e.g., blunt, so as to link to a double-strand and label either one or both strands. By employing excesses of the labeling moiety, ligation of the sample DNA may be minimized. In particular, the use of ligating enzymes such as T4 DNA ligase may be extremely desirable. As in the particular example shown below, two oligonucleotides are synthesized, at least one of which contains the label, here a dye, to be added to the nucleic acid samples. The restriction enzyme HindIII has been used in this example to produce fragments with a 5' protruding sticky end.

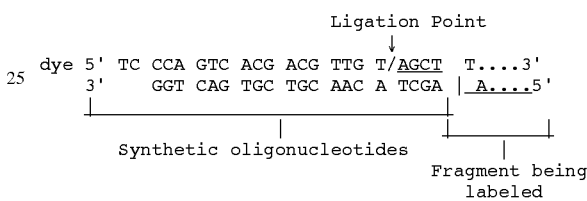

The oligonucleotides shown are synthesized so as to have sequences complementary to each other and, when hybridized to each other, to have a protruding end complementary to a sticky end of the sample nucleic acid fragment to be labeled. The synthesized oligonucleotides when hybridized to each other may have a 5' protruding end or a 3' protruding end as appropriate for a particular restriction enzyme cut site. Alternatively, the synthesized oligonucleotides may have a flush end when hybridized to each other to enable ligation to a flush ended fragment. In any case, when a ligating enzyme is added, the labeled oligonucleotide becomes covalently attached to the sample nucleic acid fragment. Furthermore, it should be noted that the synthetic oligonucleotides will not ligate to each other because no 5' phosphates are present on the synthetic pieces.

The sequence of the oligonucleotides shown in the example above was chosen so that after correct ligation occurs the recognition sequence of the enzyme is destroyed. This choice provides a unique advantage in using ligation labeling: if the cognizant restriction enzyme is present and operational during ligation, then any ligation of sample nucleic acid to itself will be re-cut. This property yields two significant advantages: first, restriction activity and ligation labeling can occur simultaneously in the same vessel thus minimizing handling and manipulations; second, a large molar excess of the labeling moiety is no longer needed to prevent sample nucleic acid from being ligated to itself. The labeling example shown can be generalized to any restriction enzyme where synthetic oligonucleotides that can be ligated into a restriction enzyme cut site to contain a sequence that destroys the recognition site of the enzyme. Such a sequence may involve a base change, e.g., from cytosine to thymidine, or perhaps substitution of a derivatized base like 5-methylcytosine, or by substitution of an analog like inosine.

In all examples above and below where restriction enzymes are used for cutting nucleic acid strands at defined recognition sequences, the use of sequence specific DNA cleaving molecules such as natural product analogs, metal ion complexes, peptide fragments, etc. is also possible, e.g. Moser and Dervan, *Science* (1987) 238:645–650, and Sluka et al., *Science* (1987) 238:1129–1132.

Kinases may be employed for phosphorylation where the phosphate group can be detected, e.g. by radioactivity.

Alkylation, e.g. methylation may be employed, where the methyl group is radioactive.

Light activated molecules which may react with individual strands may be employed. Illustrative molecules include psoralens, phenyldiazonium bisulfite, phenylazides, or the like.

DNA may be extended with a ribonucleotide, where the ribonucleotide may then be oxidized to provide an aldehyde functionality for coupling to another molecule. Conveniently, the aldehyde may be coupled with an amino-containing moiety under reductive amination conditions.

The labeling need not be direct but may be indirect. That is, the nucleic acid sequence may be modified with a molecule which may then bind to a second molecule which will provide for a detectable signal. For example, the nucleic acid sequence may be modified with biotin, where subsequently the nucleic acid sequence may be combined with avidin or streptavidin to which various detectable labels may be conjugated. Alternatively, various ligands may be used other than biotin in conjunction with their naturally occurring receptors or immunoglobulins specific for the ligand.

A wide variety of detectable labels may be used, particularly those which allow for convenient detection. The detection may be as a result of electromagnetic radiation, such as radioactivity, light absorption in the ultraviolet or visible range, fluorescence, or chemiluminescence, enzymes which produce a detectable product or destroy a detectable substrate, stable free radicals, or the like. The various molecules providing for these properties may be joined to the sequence in accordance with conventional ways, either directly or indirectly, depending upon the par- ticular manner of labeling.

As labels, various radioactive elements may be employed, such as $^{32}P$, $^{127}I$, $^{14}C$ $^{3}H$, $^{35}S$; fluorescers, such as fluorescein, rhodamine, phycobiliprotein, rare earth chelates, derivatives thereof, etc., where the fluorescers may be individual molecules or joined in tandem to a nucleic acid or non-(nucleic acid) backbone; enzymes such as horseradish peroxidase, by itself or in conjunction with glucose oxidase, urea oxidase, alkaline phosphatase, glucose-6-phosphate dehydrogenase, or the like, usually employing enzymes which react with a substrate to provide a fluorescent or light absorbing product; ligand-receptor pairs, such as biotin-avidin or streptavidin; as well as any other label which provides for detection and can be used in the subject invention.

Illustrative examples may include extending a DNA chain with a biotinyl substituted nucleotide, e.g. Bio-ll-dUTP (Enzo Biochem, Inc., New York, N.Y.), employing terminal deoxytransferase. The labeled chain would then be used in subsequent steps. For detection, avidin conjugated with a detectable label would be added, non-specifically bound avidin washed away, and the detectable label detected. Great amplification would be achieved by extending the chains with a plurality of biotinylated nucleotides. In some instances one might wish to separate the biotinylated nucleotides in the chain by employing a mixture including natural nucleotides.

Another alternative would extend a DNA chain with a ribonucleic acid employing a ligase. The resulting single strands may then be oxidized with periodate to produce a dialdehyde. The dialdehyde may be condensed with a phycoerythrin monomer or polymer to provide a fluorescent label. Alternatively, one might use nick translation or random priming with DNA polymerase to introduce a radioactive label. One might also use the polymerase chain reaction scheme (Saiki et al., *Science* (1985) 230:1350) to incorporate a radioactive or non-radioactive label on the primers or the incorporated nucleotides. For methods of labeling a nucleic acid sequence, see for example, Maniatis et al., Molecular Cloning, pp 109–132, Cold Spring Harbor Laboratory, Cold Spring Harbor, N.Y. (1982).

While for the most part, the labeled sample will be denatured to provide single-stranded DNA for contacting with the probe, labeled double-stranded DNA may also be employed by combining a probe, as described below, with a recA protein, e.g. *E. coli* recA (Honigberg et al., *Proc. Natl. Acad. Sci. USA* (1986) 83:9586–9590) and Rigas et al., *Proc. Natl. Acad. Sci. USA* (1986) 83:9591–9595. In Honigberg et al., supra, the recA protein is incubated with the probe in ATP containing (0.5–2.5 mM) buffered medium, pH 7–8, also containing an ATP-regenerating system, e.g., phosphocreatine and creatine kinase. The dsDNA and probe-recA complex are then combined and the magnesium chloride composition increased about 10-fold. In Rigas et al., the ATP-regenerating system was not utilized. The resulting duplexes may then be treated in the same way as the procedure with the single-stranded nucleic acid sample discussed below. The use of recA thus provides a means to pull out fragments of double-stranded DNA containing a sequence complementary to that of the probe without the need to denature the target DNA fragments.

Except as indicated above, the labeled denatured nucleic acid sample will be combined with the probe. The probe may be ds or ss DNA, RNA, or any other natural or synthesized nucleic acid and may be synthesized organically, enzymatically or biologically. The probe will comprise a sequence of interest for hybridizing, either homo- or heteroduplexing to the sample sequence of interest. Alternatively, the probe could be a non-nucleic acid molecule which recognizes a specific sequence, such as an antibody or a specific DNA binding protein, e.g. repressor, inducer, restriction enzyme, etc. See Dervan, *Science* (1986) 232:464–471. In addition, the probe will have a linking element for linking the probe to a solid entity, both the probe by itself or duplexed to a labeled sample chain. The linking element may take the form of a ligand or epitope which binds to an antibody or a specific receptor, a chemically reactive species, such as maleimido, which may react with a mercapto group to form a thioether, phenolic groups, which may react with diazo functionalities, aldehyde groups, which may react with amino functionalities, particularly under reductive amination conditions, or the like. The linking element could also, for example, be a nucleotide sequence that binds to its complementary sequence that is bound to the support. The particular manner in which the probe is linked to the solid entity is not critical, so long as it maintains its integrity under the subsequent conditions and does not interfere with the various stages. The binding may be covalent or non-covalent as is convenient and may, if desired, involve a concatenation of bindings, e.g. solid entity to biotin to avidin to biotin to probe or solid entity to avidin to biotin to recA to probe.

Various combinations of receptor and ligand may be employed, such as biotin with avidin or streptavidin, antibody with a hapten or antigen, a surface membrane or cytoplasm receptor with a hormone, enzyme and substrate or modified substrate, e.g., suicide inhibitor, lectin and sugar, chelate and ion, e.g., metal ion.

The probe may be prepared by any conventional technique. The probes will be synthesized and labeled employing the nick translation, ligation, or random priming methods discussed above or by using any of the commercially available nucleic acid synthesizers. Therefore, one can introduce at either terminus or along the chain, one or more groups for linking. For example, one could leave the terminal trityl group to serve as a ligand for an antibody. An RNA could be added and cleaved as previously described. A biotinylated nucleotide could be incorporated in the chain at either terminus or along the chain, resulting in a probe having one or more biotins.

The probe will usually have at least 8 nt, more usually at least 10 nt, preferably at least about 12 nt and may be 10 knt (kilonucleotides) or more, usually less than about 2 knt. The size of the probe will vary with the nature of the target sequences, amount of target sequence in the sample, and the conditions employed in the detection process.

The probe and sample will be combined together under appropriate conditions of stringency to allow for proper selection of complementary sequences. Various media may be employed, such as aqueous salt solutions, mixed solutions of water and polar organic solvents, e.g. dimethylformamide, or the like. Elevated temperatures may be employed, usually not exceeding about 110° C. for denaturation and 80° C. for hybridization. Salt concentrations will generally not exceed about 4.0M. The stringency may also be controlled by the pH of the solutions used. The stringency may be provided in the solution for contacting the probe with the sample or may be provided in subsequent washings, on and/or off the solid entity. Addition of unlabeled carrier DNA or polymers such as polyethylene glycol, heparin, dextran sulfate, etc. may be desirable to reduce binding that occurs without proper sequence homology or to accelerate reaction rates.

The duplexed probe and any unreacted probe may now be linked by means of a linking group to a separation means comprising a solid entity. The solid entity may take any of a number of convenient forms. The solid entity may conveniently be particles, naturally occurring or synthetic, e.g. polymeric particles, comprised of agarose, cellulose, Sephadex, Sepharose, polyacrylate, polystyrene, hydrophilic polymer, controlled pore glass, nylon, hydroxyethyl methacrylate (HEMA) etc., where the various supports will be functionalized in accordance with the nature of the linking element of the probe. The particles will generally be of a size in the range of about $0.5\mu$ to $100\mu$. Conveniently, the particles may be paramagnetic, so as to allow for separation by magnetic means. Where the particles are not paramagnetic, centrifugation, filtration, extraction into or between immiscible phases, electrophoretic separation, any combination of means such as centrifugation plus filtration, or other separation means may be employed. Alternatively, the solid entity may be one of any of a variety of containers, such as microtiter plate wells, microfuge tubes, microfuge tubes with integral filters, filters with absorbent pads, capillaries, columns, or the like, or combinations of solid supports. The support may be a derivatized or derivatizable surfaces or membranes, e.g. glass; nitrocellulose; derivatized nylon, e.g. Biodyne™, Pall Corp., Glen Cove, N.Y.; derivatized cellulosic polymer, e.g. Memtest™, Memtek Corp., Billerica, Mass.; or derivatized polyvinylidene difluoride, e.g. Immobilon, Millipore, Bedford, Mass., or Pall Immunoaffinity™ Membrane, Pall Corp., Glen Cove, N.Y., etc. Depending upon the nature of the solid entity, the medium will be contacted with the solid entity to provide for binding of the linking element to the solid entity. With particles, the medium may be agitated with the particles, followed by separation of the particles to produce a liquid phase supernatant and a solid particle phase. With various containers, the medium may be introduced into the container, agitated and the supernatant removed from the container. With columns or tubes, the medium may be introduced into the column or tube, contact maintained for sufficient time for a reaction to occur, and the liquid phase expelled. Using membranes or surfaces, the medium may be passed through or along the membrane or surface to permit reaction to occur and to remove unreacted species. Again, the addition of unlabeled DNA may be desirable to block binding that occurs without proper sequence homology.

The solid entity may then be treated to remove non-specific binding of labeled nucleic acid. The washings may be any of a variety of solutions which should not interfere significantly with the retention of the probe and homologous duplex on the solid entity. Thus, various aqueous buffered solutions may be employed, generally having salt concentrations below about 1.0M, pHs in the range of about 13 to 5, and at temperatures in the range of about 80° C. to 20° C. Times may vary from a few seconds to 1 hour or more. After non-specifically bound or heteroduplexed (partially complementary) labeled nucleic acid has been removed, the presence of labeled nucleic acid on the solid entity may be detected as demonstrative of the presence of a sequence complementary to the probe being present in the sample medium. At this point in the method, the labeled sample nucleic acid bound to the support should be substantially free of any unincorporated labeling molecules.

In the next step, the specifically bound labeled nucleic acid fragments are eluted from the support prior to detection. This adds yet another level of specificity to the entire process so that only the nucleic acid fragments of the desired homology to the probe are detected. Elution methods are utilized that selectively release only those labeled nucleic acids bound to the support through the probe and its linking element.

Most commonly, the labeled sample nucleic acid may be separated from the support and the probe by denaturation. Salt concentrations during this denaturation and elution process will usually be less than about 0.2 M. For efficient elution, the pH will usually be higher than 10, preferably from about 12 to 13, achieved through the use of NaOH solutions, greater than 10 mM, usually about 50–200 mM and generally less than about 300 mM in NaOH; other bases such as KOH or guanidine can also be used. Elutions may also be achieved with the use of formamide, typically between 90 and 100%, usually about 99%. Elutions can also be achieved or enhanced through denaturation by the use of elevated temperature, independently or in combination with other techniques for denaturation mentioned above. Such elevated temperatures should usually be at least 60° C., depending on the length of the probe, if temperature alone is used. Lower temperatures may suffice if chemical denaturants are used at the same time. Should the linking element be a nucleic acid, similar means would be used to release labeled target from the support.

Alternatively, the use of chemically cleavable linkages to the solid entity would permit separation of the probe-target complex from the solid entity using the appropriate cleaving agent (see, for example, Herman et al., *Analytical Biochem.* (1986) 156:48–55). Elution may also be achieved through the use of conditions that disrupt ligand receptor interactions, e.g., by the introduction of denaturing conditions such as 100 mM NaOH at an elevated temperature of at least 40° C. or by flooding the system with a compound that competes with the ligand labeled probe for the ligand binding site. As another alternative, changing ion concentrations may result in the release of a protein DNA complex (see Honigberg et al., supra). Still another alternative will allow the use of reagents such as glyoxal which chemically modifies DNA or RNA in such a fashion as to break up and prevent the complementary binding of two nucleic acid strands (e.g., Carmichael and McMaster, *Methods of Enzymology*, (1980) 65:380–391).

The eluted labeled nucleic acid may then be detected in accordance with conventional techniques. Alternatively, the eluted labeled nucleic acid will be subjected to sizing before final detection. This sizing step not only yields specific and important information about the fragments of interest but it also provides yet another level of discrimination against non-specific or partially homologous labeled nucleic acid that has been eluted from the support. Sizing may be performed by electrophoresis, gradient density centrifugation, liquid chromatography, or the like. The presence of the label allows for detection of the band(s) and standards may be employed for size comparison. It may be desirable to carry out the size separation where the nucleic acid is in a denatured state, where such denaturation is achieved by pH, glyoxal or similar derivatizing treatments, use of strong hydrogen bonding agents, or the like. Conveniently, the standards may be labeled with a contrasting label, for example a dye or fluorescer providing for a signal at a different wavelength from the signal obtained with the labeled sample. In this way, the comparison is simplified and the relationship between the standard and sample is readily determinable. An instrument such as a densitometer or gel scanner or an automated fluorescent gel electrophoresis scanner apparatus such as the ABI Model 370, Applied Biosystems Inc., Foster City, Calif., may be employed to measure band intensities and position. Alternatively, the image may be recorded photographically with the appropriate stains.

It may be noted here that the procedures described above can yield all the information normally acquired from a Southern blot or other similar technique that involves size separation, transfer, and subsequent probing. The invention allows determination of the lengths of nucleic acid fragments to which a probe binds without any blotting steps, without gel manipulations, without large volumes of probe and wash solution, and without hybridization on a solid support (thus allowing more rapid kinetics and less opportunity for background and non-specific binding). Thus, the subject invention is much more amenable to automation than the conventional Southern blot procedure.

The supernatant remaining after separation of the solid and liquid phases may be repeatedly probed with different probes to detect other sequences. In this manner one could detect the presence of alleles, pseudogenes, lesions in multicopy genes, germline rearrangements, or the like or even completely independent sequences.

The following examples are offered by way of illustration and not by way of limitation.

EXPERIMENTAL

EXAMPLE 1

Use of a photochemically driven reaction to label a probe with the ligand biotin.

1. Following the manufacturer's directions, Photoprobe™ biotin (Vector Laboratories, Burlingame, Calif.) is reconstituted to a 1 mg/ml concentration in distilled water.

2. After phenol-chloroform extraction and ethanol precipitation (see Maniatis et al., supra) the nucleic acid sample is dissolved in 0.1 mM EDTA to a final concentration of 1 $\mu g/\mu l$.

3. An equal volume of the reconstituted Photoprobe™ Biotin is added to the dissolved nucleic acid and then irradiated on ice 10 cm beneath a General Electric Model #RSM, 275 Watt sunlamp for 15 minutes.

4. 0.1M Tris-HCl, pH 9.0 is then added to make a total volume of 100 $\mu l$. Carrier DNA, such as salmon sperm DNA is added, if the total amount of DNA is less than 10 $\mu g$.

5. 2-Butanol (100 $\mu l$) is added, the mixture agitated mildly, centrifuged briefly and the upper phase discarded. This extraction is repeated a second time.

6. 5M NaCl (0.6 $\mu l$) and 100 $\mu l$ of 95% ethanol is added, the mixture mildly agitated, and allowed to stand in the dark for 1 hour to form a precipitate. The mixture is centrifuged, the resulting pellet rinsed with 70% ethanol, residual solvent removed in a vacuum centrifuge, and the pellet resuspended to a volume in a buffer for subsequent use of the labeled probe.

EXAMPLE 2

Use of ligation to label a probe with the ligand biotin.

1. Oligodeoxynucleotides with structures I and II are synthesized on an Applied Biosystem Model 381A DNA synthesizer according to the manufacturer's directions. Structure I is synthesized with C (cytosine) in the X positions shown. The C's are then converted to the structure of X shown by a transamination reaction performed as described by Draper, *Nucleic Acids Research* (1984) 12:988 ff, followed by reaction with long chain arm biotin according to the manufacturer's directions (Pierce Chemical Co., Rockford, Ill.).

2. A reaction mixture is prepared by combining the following reagents:

1 $\mu l$ of 1 pmole/$\mu l$ of pSP64 plasmid (Promega, Madison, Wis.) in 10 mM Tris HCl, 1 mM EDTA, pH 8.0 (TE)

1 $\mu l$ of 10×Medium Salt Buffer (Maniatis et al., supra)

1 $\mu l$ of 10 mM ATP

1 $\mu l$ of 1 unit/$\mu l$ T4 ligase (Boehringer Mannheim, Indianapolis, Ind.)

1 $\mu l$ of biotinylated oligodeoxynucleotide (Structure I containing 2.5 pmole in TE)

1 $\mu l$ of complementary oligodeoxynucleotide (Structure II containing 2.5 pmoles in TE)

3 $\mu l$ water

1 $\mu l$ of 10 units/$\mu l$ HindIII restriction enzyme (Boehringer Mannheim, Indianapolis, Ind.)

3. The mixture is incubated for 1 hour at 37° C.

4. The reaction is stopped by adding 1 $\mu l$ of 0.2M EDTA.

Structure I

5'>TXXXTTTTTTTTTTTTAGTTATGATGTTGT<3'

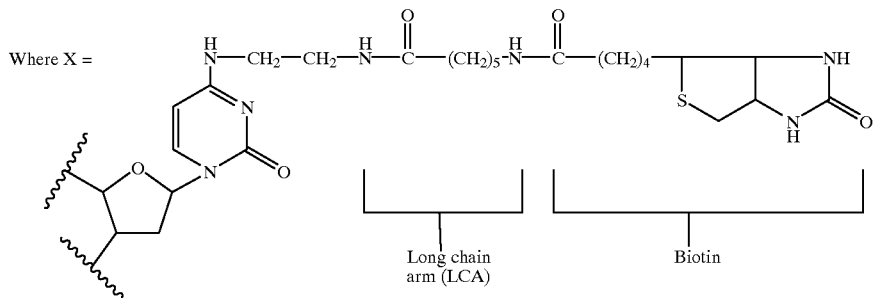

Where X =

Long chain arm (LCA) | Biotin

Structure II

5'-AGCTACAACATCATAACT

This example utilizes the restriction enzyme HindIII. It may be advantageous in some situations to use a restriction enzyme such as AluI that cuts more frequently so as to produce a probe consisting of shorter fragments which would result in more rapid hybridization kinetics. Use of a different restriction enzyme usually may necessitate different buffer conditions as well as the use of oligonucleotides consistent with the restriction recognition site of such enzyme.

EXAMPLE 3

Use of random priming to label a probe with the ligand biotin.

1. Random sequence hexamers are synthesized on an Applied Biosystems Model 381A DNA Synthesizer according to manufacturer's directions. The hexamers are synthesized with complete degeneracy of all 4 bases at each position in the hexamer. The hexamers are then capped with Amino-Link™ and purified according to the manufacturer (Applied Biosystems). The hexamers are then labeled with long chain arm biotin (Pierce Chemical) according to manufacturer's directions, producing Structure III.

Structure III

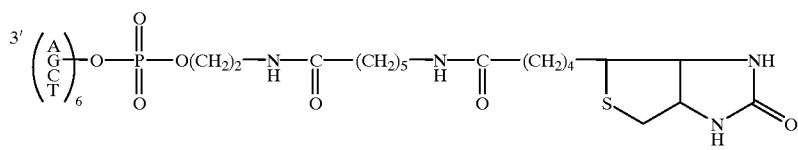

2. A mixture is prepared as follows:

1 μl lamdba HindIII restriction fragments at 10 ng/μl in TE which has been boiled 10 minutes and quenched on ice 1.5 μl 1:1:1 mix of 0.5 mM dGTP, dCTP, and dTTP 2.0 μl 5×random priming buffer (Feinberg and Vogelstein, Anal. Biochem (1983) 132:6–13, and Feinberg and Vogelstein, Anal. Biochem (1984) 137:266–267)

2.0 μl of the biotin hexamer shown in Structure III (2.5 μg/μl in H$_2$O)

2.5 μl of 10 μCi/μl AT$^{32}$P (Dupont NEN, Wilmington, Del.)

0.5 μl water 0.5 μl of E. coli Polymerase I Klenow fragment, 7 units/μl from Bethesda Research Labs 3. Incubate 30 minutes at 37° C.

4. Remove excess random primers and nucleotides by use of a Sephadex G-50 BioSpin column (5 PRIME→3 PRIME, Inc., Paoli, Pa.) according to manufacturer's directions.

5. An aliquot of the purified mixture is run on an 8% polyacrylamide gel and autoradiographed. Successful random priming is observed by the presence of high molecular weight radioactive material.

EXAMPLE 4

Use of ligation to label sample nucleic acid with fluorescent dyes.

1. Using an Applied Biosystem Model 381 DNA synthesizer, an 18 nucleotide oligomer is synthesized and purified following the manufacturer's directions. The 5' end is terminated with an amino group using Amino-Link™ (Applied Biosystems). This amino group is coupled to fluorescein N-hydroxy succinimide, again according to the manufacturer's directions (Applied Biosystems).

2. Using an Applied Biosystems Model 381 DNA synthesizer, a 20 nucleotide oligomer is synthesized and purified following the manufacturer's directions. The synthesized sequence is

5' AGC TAC AAC GTC GTG ACT GG 3'

The sequence is chosen so that the first 14 nucleotides (from the 5' end) are complementary to the 3' end of the fluorescein labeled 18-mer and the four nucleotides at the 3' end of the 18 mer are complementary to the 5' sticky end overhang generated by the restriction enzyme HindIII. The particular sequence chosen will destroy the recognition sequence of HindIII when the 18-mer/20-mer duplex is formed and then is ligated to the sticky ends of target DNA that has been cut with the HindIII restriction enzyme.

3. A reaction mixture is prepared by mixing the following reagents:

1 μg of target DNA in 1 μl of water 0.9 µl of 10×HindIII reaction buffer (BRL Gaithersberg, Md.)

3.0 µl of the 18-mer in water; the number of moles should be twice that of the expected number of sticky ends generated when the HindIII digests the 1 µg of target DNA.

2.0 µl of the 20-mer in water; the number of moles should be equal to that of the 18-mer.

1.0 µl of 10 mM dithiothreitol 1.0 µl of 3 mM ribose ATP 0.5 µl of HindIII enzyme (12 units/µl)

0.5 µl of ligase enzyme (0.5 units)

4. Incubate at 37° C. for 1 hour.

5. Add 0.5 µl of 0.2M EDTA and 1.0 µl of 20 µg/ul of glycogen in water.

6. Clean up mixture by performing two phenol/chloroform extractions. Add 10 µl each of phenol and chloroform. Mix and centrifuge. Remove and discard lower phase. Repeat. (Maniatis et al., supra).

7. Add ≧1 µl 3M NaAc pH 5.5 and 25 µl of 95% ethanol. Mix. Let stand for 30 minutes. Centrifuge.

8. Wash the precipitate with 500 µl of 70% ethanol.

9. Use a vacuum centrifuge to dry sample.

10. Resuspend in 50 µl of 10 mM Tris, 1 mM EDTA, pH 8.0.

11. An aliquot of the reaction mixture is applied to a 0.6% agarose gel run at 3 volts/cm in 1×TBE (Tris-borate EDTA) buffer for 4 hours. The fluorescent bands migrating through the gel are detected by an Applied Biosystem 370A DNA sequencer adapted to read horizontal agarose gels. If lambda phage DNA is used as target, fluorescent peaks are detected corresponding to the 560, 2027, 2322, 4361, 6557, 9416, and 23,130 base pair fragments in the HindIII cut lambda DNA. (The presence of the cos site in lambda will result in ligation of the 4361 base pair fragment to the 23,130 base pair fragment.)

EXAMPLE 5

Use of kinase enzyme to radioactively label sample nucleic acid.

Dephosphorylated DNA (alkaline phosphatase treated) rigorously purified by gel electrophoresis (5' ends 1–50 pmoles) 5 µl 10× kinase buffer I, 50 pmoles (150 µCi([γ-$^{32}$P]ATP, 10–20 units T4 polynucleotide kinase and water to 50 µl are mixed and incubated at 37° C. for 30 min. To the mixture is added 2 µl of 0.5 molar EDTA and the mixture extracted with phenol/chloroform, followed by DNA precipitation with ethanol. The DNA is redissolved in 50 µl TE and the labelled DNA separated from unincorporated [γ-$^{32}$P] ATP by G-25 spin column chromatography. (Maniatis et al., supra).

EXAMPLE 6

Use of photobiotinylated RNA probes and radioactively labeled sample DNA to detect specific restriction fragments and establish their lengths.

1. Sample DNA consisting of lambda DNA and pGEM-3 DNA (Promega, Madison, Wis.) are both cut with HindIII restriction enzyme and then are labeled with $^{32}$P as described in Example 5.

2. Avidin-coated magnetic beads (Advanced Magnetics, Cambridge, Mass.) are washed three times with 0.2M NaCl, 0.01M Tris, 0.001M EDTA, pH 8.0 and are then resuspended at a concentration of 16% packed beads per 300 µl in the washing buffer with 1 µg/µl dextran sulfate.

3. An RNA transcript of pGEM-3 is prepared according to the manufacturer's directions (Promega Biotech) for use as the probe. The probe RNA is then labeled with biotin photochemically as described in Example 1. The probe RNA is resuspended in TE at a concentration of 160 ng/µl.

4. The sample DNA mixture is then probed for specific pGEM-3 DNA using the biotinylated pGEM-3 RNA probe by preparing the following mixture in a 1.5 ml polypropylene tube:

74.5 µl formamide 8.0 µl 5M NaCl 2.0 µl photobiotinylated probe RNA at a concentration of 160 ng/µl in TE 0.5 µl $^{32}$P-labeled pGEM-3 DNA at a concentration of 8 ng/µl 7.5 µl containing 3 ng of $^{32}$P-labeled lambda (HindIII cut) DNA in TE 3.0 µl (1 µg/µl) sheared, denatured and quenched salmon sperm DNA 4.0 µl 1M citrate-phosphate buffer pH 6.4

0.5 µl 200 mM EDTA

The volume is then brought to 100 µl with water.

5. The mixture is then denatured by suspending the tube of mixture into a boiling water bath for 4 minutes.

6. The mixture is then cooled to 45° C. and then held at 45° C. for a 2 hour incubation.

7. A 25 µl aliquot of the hybridization mixture is then diluted in 1 ml of 200 mM NaCl, 10 mM Tris, 1 mM EDTA, pH 8.0.

8. 50 µl of magnetic beads are then added, shaken gently, and allowed to incubate for 40 minutes.

9. Following the manufacturer's directions, the beads are separated from the solution and the supernatant is removed.

10. The beads are then washed twice with 200 mM NaCl in TE buffer at room temperature to remove any loosely bound material by repeated resuspension, magnetic separation, and removal of supernatant.

11. The beads are then resuspended in 100 µl of 200 mM NaOH to release the target DNA by denaturing the RNA-DNA duplex and by scission of the RNA. The released material is then precipitated by the addition of 1 µl of 20 µg/µl glycogen plus 10 µl of 3.0 M NaAc pH 5.5 plus 250 µl of 95% ethanol. After mixing, the precipitate is spun out for 10 min. in an Eppendorf Microfuge™ at maximum speed, washed with 500 µl of 70% ethanol, dried in a Savant Speed Vac™, and then the pellet is resuspended in alkaline loading buffer (Maniatis et al., supra).

12. The alkaline agarose gel, 0.7% agarose, is prepared as described by Maniatis et al., supra, p. 171 ff. Aliquots of the sample mixture, the supernatant, and the eluant are applied to the gel and run for 3 hours at 8 volts/cm. The gel is then dried and autoradiographed. In the lanes containing the sample mixture, all the various fragments are present. In the lanes containing the supernatant, the pGEM-3 RNA probe has been largely removed. In the lanes containing the eluant, the 2.9 kb pGEM-3 DNA, the fragment pulled out specifically by the RNA probe, is the only significant band that appears. The procedures used thus result in the specific detection of the fragment complementary to the probe and the measurement of the length of such fragment(s).

EXAMPLE 7

Use of photobiotinylated RNA probes to detect specific fragments of sample DNA that have been fluorescently labeled by ligation.

1. A RNA probe labeled with biotin is prepared as described in Examples 1 and 6.

2. A sample consisting of 6 femtomoles of lambda DNA and 100 attomoles of pGEM-3 DNA is cut by HindIII restriction enzyme and then labeled with fluorescein by ligation as described in Example 4 with amounts scaled as appropriate.

3. Denaturation of sample and probe, hybridization, separation, washing, and elution are performed as described in Example 6 except as follows: All solutions contain 1% Tween 20 and 0.1 µg/µl dextran sulfate; the first two washes are done with 1M NaCl in TE buffer; three additional washes are performed with 0.1×SSPE prior to elution; the beads used are streptavidin-agarose from a stock containing 50% packed beads (Pierce Chemical); and centrifugation is used to separate the beads since they are not magnetic.

4. An alkaline agarose gel, 0.6% agarose is prepared as described by Maniatis et al., supra, p. 171 ff. Aliquots of dilutions of the sample mixture, the supernatant, and the eluant are applied to the gel and run for 4 hours at 3 volts/cm. The fluorescent bands migrating through the gel are detected by an Applied Biosystems Model 370 DNA Sequencer adapted to read horizontal agarose gels.

5. In the lanes containing the sample mixture, all the various fragments are proportionately present. In the lanes containing the supernatant, the pGEM-3 RNA probe removes half of the pGEM-3 DNA corresponding to the strand complementary to the probe. In the lanes containing the eluant, the 2.9 kb pGEM-3 DNA, the fragment complementary to the RNA probe, is the most significant band that appears. The procedures thus result in the specific detection of the fragment complementary to the probe and the measurement of the length of such fragment(s).

EXAMPLE 8

Use of DNA probe labeled with biotin by ligation to detect specific fragments of DNA that have been fluorescently labeled by ligation.

1. A DNA probe consisting of a pGEM-3 plasmid (Promega) is labeled with biotin by ligation as described in Example 2.

2. A sample consisting of 6 femtomoles of lambda DNA and 100 attomoles of pGEM-3 DNA is cut by HindIII restriction enzyme and then labeled with fluorescein by ligation as described in Example 4 with amounts scaled as appropriate.

3. Two femtomoles of probe DNA in addition to the sample are denatured in 200 µl of 1.5×SSPE with 1% Tween 20 and 0.1 µg/µl of dextran sulfate at 95° C. for 5 minutes followed by a 65° C. hybridization for two hours; 20 µl of the 50% streptavidin-agarose bead suspension are added and the mixture incubated at 37° C. for 1 hour.

4. Separation, washing, and elution are performed as described in Example 7. An alkaline agarose gel, 0.6% agarose is prepared as described by Maniatis et al., supra, p. 171 ff. Aliquots of the sample mixture, the supernatant, and the eluant are applied to the gel and run for 4 hours at 3 volts/cm. The fluorescent bands migrating through the gel are detected by an Applied Biosystems Model 370 DNA Sequencer adapted to read horizontal agarose gels.

5. In the lanes containing the sample mixture, all the various fragments are present in appropriate amounts. In the lanes containing the supernatant, the pGEM-3 probe removes most of the target pGEM-3 DNA. In the lanes containing the eluant, the pGEM-3 DNA, the fragment pulled out specifically by the pGEM-3 probe, is the most significant band that appears. The procedures thus result in the specific detection of the fragment complementary to the probe and the measurement of the length of such fragment(s).

EXAMPLE 9

Use of magnetic beads coated with streptavidin and DNA probe labeled with biotin to detect specific fragments of DNA that have been fluorescently labeled by ligation.

1. A DNA probe consisting of a pSP64 plasmid (Promega) is labeled with biotin by ligation as described in Example 2 except that AluI restriction enzyme is used instead of HindIII and buffer conditions are adjusted appropriately. TE with 1% Tween 20 is added to adjust the concentration of probe to 9 femtomoles of each pSP64 plasmid fragment per 10 ul.

2. A sample consisting of 100 femtomoles of lambda DNA and 100 attomoles of pSP64 DNA is cut by HindIII restriction enzyme, labeled with fluorescein by ligation as described in Example 4 (with amounts scaled as appropriate) and then diluted with TE containing 1% Tween 20 to a total volume of 90 ul.

3. Sample and probe are combined in a hybridization mixture as follows:

90 ul of sample from step 2 above 10 ul of probe from step 1 above 14 ul of formamide 37 ul of an aqueous solution which is 2.0 M sodium phosphate pH 7.0, 0.1% sodium lauryl sulfate and 1 ug/60 ul dextran sulfate 4. The hybridization mixture is incubated at 102° C. for 10 minutes to denature the sample and probe and then allowed to incubate for 20 minutes at 65° C. for hybridization to occur. The sample is then cooled to 37° C. and 20 ul of a 5 mg/ml suspension of streptavidin-coated magnetic beads (Advanced Magnetics, Cambridge, Mass.) are added and the mixture is allowed to incubate for another 15 minutes at 37° C. (Beads are prewashed two times in 0.5×SSPE containing 1% Tween 20, 1 ug/60 ul dextran sulfate, and 0.1% sodium lauryl sulfate.)

5. The magnetic beads are separated magnetically per manufacturer's directions, the supernatant is removed, and then the beads are washed as follows:

5 washes of 0.5 ml each at 65° C. with 1×SSPE containing 1% Tween 20, 1 ug/60 ul dextran sulfate, and 0.1% sodium lauryl sulfate 2 washes of 0.5 ml each at 65° C. with 0.1×SSPE containing 1% Tween 20, 1 ug/60 ul dextran sulfate, and 0.1% sodium lauryl sulfate 1 wash of 0.5 ml at room temperature of 0.1×SSPE 6. After the final wash solution is removed, the beads are resuspended in 6 ul of a mixture which is 100 mM NaOH, 5% Ficoll, and 0.3 ug/ul of dextran sulfate. After 10 minutes, the bead suspension is directly loaded into the well of an alkaline agarose gel. Conditions for running the gel and detecting the bands are the same as in Example 8.

7. In the lane of the gel in which the beads were loaded, only the fragments of pSP64 are detected. None of the fragments corresponding to the lambda DNA is detected. The entire procedure thus results in the specific detection of only the fragments complementary in structure to the probe.

It is evident from the above results, that the subject method provides for an accurate sensitive and rapid technique for detecting low levels of a nucleic acid sequence, particularly in a complex mixture. In addition, in many instances, where the size of the sequence is of interest, the method allows for isolation of the labeled sample and determination of size. The method is extremely flexible and allows for automation, so that technician error can be substantially obviated. In addition, the method can be modified to vary the label and method of linking to the support, so that various conditions and samples may be addressed. Furthermore, the steps allow for substantial removal of all interfering materials, as well as non-specific binding materials so as to provide for a highly accurate and sensitive assay with a high degree of reliability.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting a nucleic acid sequence comprising:

labeling nucleic acid suspected of having a sequence of interest with a label;

combining in solution, said nucleic acid with a probe comprising a sequence complementary to said sequence of interest and a coupling means for binding to a separation means for separating said probe and complexes from non-complementary sequences, said combining under conditions to form complexes between said sequence of interest and said sequence capable of specifically binding, with the proviso that when said nucleic acid is in double stranded form, a nucleic acid probe is complexed with a recA protein;

separating said probe and said complexes from non-complementary sequences with said separation means;

releasing said labeled nucleic acid from said separation means to provide unbound labeled nucleic acid;

size separating said unbound nucleic acid; and detecting said size separated unbound labeled nucleic acid by means of said label.

2. A method according to claim 1, wherein said size separating employs electrophoresis.

3. A method according to claim 1, wherein said labeled nucleic acid is released by denaturing said complexes.

4. A method according to claim 1, wherein said separation means comprises paramagnetic particles, agarose particles, cellulosic particles, or synthetic polymeric particles.

5. A method according to claim 1, wherein said coupling means comprises a member of a specific binding pair and said separation means comprises the complementary member of said specific binding pair.

6. A method according to claim 5, wherein said separation means comprises paramagnetic particles to which are bound said complementary member.

7. A method for detecting a nucleic acid sequence of interest in a sample comprising genomic DNA, said method comprising:

fragmenting said genomic DNA to provide nucleic fragments of less than about 50 kbp;

labeling said nucleic acid fragments with a label;

combining in solution, said nucleic acid fragments in single stranded form with a probe comprising a nucleic acid sequence complementary to said sequence of interest and a coupling means for binding to particles capable of binding to said coupling means, said combining under hybridizing conditions to form duplexes between said sequence of interest and said sequence capable of specifically binding;

separating said probe and duplexes from non-complementary sequences with said particles;

releasing said labeled nucleic acid from said particles by chemical and/or thermal denaturation;

size separating said released labeled nucleic acid;

and detecting said size-separated nucleic acid.

8. A method according to claim 7, wherein said size separating employs electrophoresis.

9. A method according to claim 8, wherein said labeling comprises ligating said DNA fragments with double stranded RNA labeled molecules having a terminus complementary to a terminus of said DNA fragments.

10. A method according to claim 7, wherein said labeling comprises ligating said DNA fragments with dsDNA labeled molecules having a terminus complementary to a terminus of said DNA fragments.

11. A method according to claim 10, wherein said complementary terminus of said DNA fragments is produced by restriction enzyme digestion of a restriction site and said ligating of said complementary terminus results in a sequence other than the sequence cleaved by said restriction enzyme.

12. A method according to claim 11, wherein said complementary terminus of said DNA fragments is blunt ended.

13. A method according to claim 7, wherein said labeling comprises extending the chains of said DNA fragments with a labeled nucleotide.

14. A method according to claim 7, wherein said label is a radionuclide, fluorescer, chemiluminescer, ligand of a specific binding pair or enzyme.

15. A method according to claim 7, wherein said coupling entity comprises a receptor and ligand combination.

16. A method according to claim 15, wherein said receptor and ligand combination consists essentially of avidin or streptavidin and biotin; antibody and hapten or antigen; complementary strands of nucleic acid; receptor and hormone; lectin and sugar; or chelate and ion.

17. A kit comprising a nucleic acid sequence joined to a linking entity, a solid component capable of specifically binding said linking entity, reagents for labeling a nucleic acid sequence, and means for sizing nucleic acid fragments.

18. A kit according to claim 17, wherein said linking entity is a member of a specific binding pair, said solid component comprises the complementary member of said specific binding pair, said reagents comprise a labeled nucleotide, and said sizing means comprises an electrophoretic gel.

19. A kit according to claim 18, wherein said specific binding pair consists of a receptor and ligand combination which consists essentially of avidin or streptavidin and biotin; antibody and hapten or antigen; complementary strands of nucleic acid; receptor and hormone; lectin and sugar; or chelate and ion.

* * * * *